United States Patent
Shalev

(10) Patent No.: US 8,951,298 B2
(45) Date of Patent: Feb. 10, 2015

(54) ENDOVASCULAR SYSTEM WITH CIRCUMFERENTIALLY-OVERLAPPING STENT-GRAFTS

(75) Inventor: Alon Shalev, Ra'anana (IL)

(73) Assignee: Endospan Ltd., Herzilyia Pituach (IL)

( * ) Notice: Subject to any disclaimer, the term of this patent is extended or adjusted under 35 U.S.C. 154(b) by 0 days.

(21) Appl. No.: 13/807,906

(22) PCT Filed: Jun. 19, 2012

(86) PCT No.: PCT/IL2012/000241
§ 371 (c)(1),
(2), (4) Date: Feb. 8, 2013

(87) PCT Pub. No.: WO2012/176187
PCT Pub. Date: Dec. 27, 2012

(65) Prior Publication Data
US 2013/0204343 A1    Aug. 8, 2013

Related U.S. Application Data

(60) Provisional application No. 61/499,195, filed on Jun. 21, 2011.

(51) Int. Cl.
*A61F 2/06* (2013.01)
*A61F 2/852* (2013.01)
(Continued)

(52) U.S. Cl.
CPC . *A61F 2/852* (2013.01); *A61F 2/07* (2013.01); *A61F 2/962* (2013.01);
(Continued)

(58) Field of Classification Search
CPC ....... A61F 2/07; A61F 2002/072; A61F 2/92; A61F 2/89; A61F 2250/0063; A61F 2250/0064

USPC ........... 623/1.11, 1.16, 1.35, 1.23, 1.36, 1.21, 623/1.3

See application file for complete search history.

(56) References Cited

U.S. PATENT DOCUMENTS 4,355,426 A    10/1982    MacGregor
4,505,767 A    3/1985     Quin
(Continued)

FOREIGN PATENT DOCUMENTS

CA    2 497 704       3/2004
CN    201058061 Y     5/2008
(Continued)

OTHER PUBLICATIONS

"E-vita® open plus" product brochure (JOTEC GmbH, Hechingen, Germany) (2010).
(Continued)

*Primary Examiner* — Darwin Erezo
*Assistant Examiner* — Sidharth Kapoor
(74) *Attorney, Agent, or Firm* — Sughrue Mion, PLLC

(57) ABSTRACT

A multi-component endovascular stent-graft system (10) includes a body portion (16), which includes a plurality of stent-grafts (20), which include: (a) respective stent members (22), which are shaped, when the stent-grafts (20) are in respective radially-expanded states, so as to define respective tubes, each of which is circumferentially complete at at least one longitudinal location therealong; and (b) respective graft members (24), which circumscribe respective circumferential arcs (40) of the respective stent members (22). The circumferential arcs (40) have respective extents that are less than entire circumferences of the respective stent members (22) at least partially along respective axial lengths of the stent members (22).

31 Claims, 12 Drawing Sheets

(51) Int. Cl.
*A61F 2/07* (2013.01)
*A61F 2/962* (2013.01)
*A61F 2/848* (2013.01)
*A61F 2/89* (2013.01)

(52) U.S. Cl.
CPC .. *A61F 2002/075* (2013.01); *A61F 2002/8486* (2013.01); *A61F 2230/0091* (2013.01); *A61F 2250/0063* (2013.01); *A61F 2/89* (2013.01)
USPC ........ 623/1.11; 623/1.16; 623/1.21; 623/1.13

(56) References Cited

U.S. PATENT DOCUMENTS

| | | | |
|---|---|---|---|
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,234,448 A | 8/1993 | Wholey et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,980,552 A | 11/1999 | Pinchasik et al. |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,059,824 A | 5/2000 | Taheri |
| 6,099,497 A | 8/2000 | Adams et al. |
| 6,117,145 A | 9/2000 | Wood et al. |
| 6,132,457 A * | 10/2000 | Chobotov ............ 623/1.13 |
| 6,156,064 A | 12/2000 | Chouinard |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,312,458 B1 | 11/2001 | Golds |
| 6,325,823 B1 | 12/2001 | Horzewski et al. |
| 6,344,056 B1 | 2/2002 | Dehdashtian |
| 6,428,565 B1 | 8/2002 | Wisselink |
| 6,506,211 B1 | 1/2003 | Skubitz et al. |
| 6,520,988 B1 | 2/2003 | Colombo et al. |
| 6,613,078 B1 | 9/2003 | Barone |
| 6,635,083 B1 | 10/2003 | Cheng et al. |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,743,195 B2 | 6/2004 | Zucker |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,198,638 B2 | 4/2007 | Dong |
| 7,201,772 B2 | 4/2007 | Schwammenthal |
| 7,223,266 B2 | 5/2007 | Lindenbaum et al. |
| 7,279,003 B2 | 10/2007 | Berra et al. |
| 7,294,145 B2 | 11/2007 | Ward |
| 7,306,623 B2 | 12/2007 | Watson |
| 7,341,598 B2 | 3/2008 | Davidson et al. |
| 7,407,509 B2 | 8/2008 | Greenberg et al. |
| 7,429,269 B2 | 9/2008 | Schwammenthal |
| 7,438,721 B2 | 10/2008 | Doig |
| 7,442,204 B2 | 10/2008 | Schwammenthal |
| 7,473,272 B2 | 1/2009 | Pryor |
| 7,491,231 B2 | 2/2009 | Nazzaro |
| 7,537,609 B2 | 5/2009 | Davidson et al. |
| 7,540,881 B2 | 6/2009 | Meyer et al. |
| 7,544,160 B2 | 6/2009 | Gross |
| 7,637,939 B2 | 12/2009 | Tischler |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,722,626 B2 | 5/2010 | Middleman et al. |
| 7,731,732 B2 | 6/2010 | Ken |
| 7,803,178 B2 | 9/2010 | Whirley et al. |
| 7,806,923 B2 | 10/2010 | Moloney |
| 7,815,673 B2 | 10/2010 | Bloom et al. |
| 7,887,575 B2 | 2/2011 | Kujawski |
| 7,955,374 B2 * | 6/2011 | Erickson et al. ............ 623/1.16 |
| 7,959,662 B2 | 6/2011 | Erbel et al. |
| 8,066,755 B2 | 11/2011 | Zacharias et al. |
| 8,080,053 B2 | 12/2011 | Satasiya et al. |
| 8,172,892 B2 | 5/2012 | Chuter et al. |
| 2001/0004705 A1 | 6/2001 | Killion et al. |
| 2001/0014823 A1 | 8/2001 | Resseman et al. |
| 2001/0034550 A1 | 10/2001 | Buirge et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0053930 A1 | 12/2001 | Kugler et al. |
| 2002/0040236 A1 | 4/2002 | Lau et al. |
| 2002/0099438 A1 | 7/2002 | Furst |

(56) References Cited

U.S. PATENT DOCUMENTS

| | | |
|---|---|---|
| 2002/0099441 A1 | 7/2002 | Dehdashtian |
| 2002/0107564 A1 | 8/2002 | Cox et al. |
| 2002/0123791 A1 | 9/2002 | Harrison |
| 2002/0156495 A1 | 10/2002 | Brenneman et al. |
| 2003/0040791 A1 | 2/2003 | Oktay |
| 2003/0074055 A1 | 4/2003 | Haverkost |
| 2003/0093145 A1 | 5/2003 | Lawrence-Brown et al. |
| 2003/0130720 A1 | 7/2003 | DePalma et al. |
| 2003/0144725 A1 | 7/2003 | Lombardi |
| 2003/0153968 A1 | 8/2003 | Geis et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0133266 A1 | 7/2004 | Clerc et al. |
| 2004/0171978 A1 | 9/2004 | Shalaby |
| 2004/0181149 A1 | 9/2004 | Langlotz et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0149166 A1 | 7/2005 | Schaeffer et al. |
| 2005/0154448 A1 | 7/2005 | Cully et al. |
| 2005/0171598 A1 | 8/2005 | Schaeffer |
| 2005/0203606 A1 | 9/2005 | VanCamp |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0266042 A1 | 12/2005 | Tseng |
| 2005/0283188 A1 | 12/2005 | Loshakove et al. |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0100684 A1 | 5/2006 | Elliott |
| 2006/0106406 A1 | 5/2006 | Weinberger |
| 2006/0149360 A1 | 7/2006 | Schwammenthal |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0281966 A1 | 12/2006 | Peacock, III |
| 2007/0021822 A1 | 1/2007 | Boatman |
| 2007/0043425 A1 | 2/2007 | Hartley et al. |
| 2007/0050011 A1 | 3/2007 | Klein et al. |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Menardiere et al. |
| 2007/0156167 A1 | 7/2007 | Connors et al. |
| 2007/0167898 A1 | 7/2007 | Peters et al. |
| 2007/0167955 A1 | 7/2007 | Menardiere et al. |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0097578 A1* | 4/2008 | Erickson et al. ............ 623/1.16 |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0195190 A1 | 8/2008 | Bland et al. |
| 2008/0195191 A1 | 8/2008 | Luo et al. |
| 2008/0215134 A1 | 9/2008 | Lawrence/Brown |
| 2008/0249598 A1 | 10/2008 | Sherry |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0300665 A1 | 12/2008 | Lootz et al. |
| 2008/0319528 A1 | 12/2008 | Yribarren et al. |
| 2009/0012597 A1* | 1/2009 | Doig et al. ............... 623/1.13 |
| 2009/0012602 A1 | 1/2009 | Quadri |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069882 A1 | 3/2009 | Venturelli et al. |
| 2009/0082841 A1 | 3/2009 | Zacharias et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0070019 A1 | 3/2010 | Shalev |
| 2010/0082091 A1 | 4/2010 | Berez et al. |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0292774 A1 | 11/2010 | Shalev |
| 2010/0318171 A1 | 12/2010 | Porter et al. |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval |
| 2011/0208298 A1 | 8/2011 | Tuval |
| 2011/0218607 A1 | 9/2011 | Arbefeuille et al. |
| 2011/0264184 A1 | 10/2011 | Heltai |
| 2012/0310324 A1* | 12/2012 | Benary et al. ............... 623/1.12 |

FOREIGN PATENT DOCUMENTS

| | | |
|---|---|---|
| EP | 1177780 A2 | 2/2002 |
| EP | 1325716 A1 | 7/2003 |
| EP | 2 298 248 A1 | 3/2011 |
| JP | 2002-253682 | 9/2002 |
| WO | 2004/017868 | 3/2004 |
| WO | 2005/002466 | 1/2005 |

(56) References Cited

FOREIGN PATENT DOCUMENTS

| WO | 2005/037138 | 4/2005 |
|---|---|---|
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010/128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |
| WO | 2011/106532 | 9/2011 |
| WO | 2011/106533 | 9/2011 |
| WO | 2011/106544 | 9/2011 |
| WO | 2012/049679 | 4/2012 |
| WO | 2012/104842 | 8/2012 |
| WO | 2012/111006 | 8/2012 |
| WO | 2012/117395 | 9/2012 |

OTHER PUBLICATIONS

An English Translation of an Office Action dated Aug. 25, 2011, which issued during the prosecution of Chinese Patent Application No. 200880014919.9.

Fonseca A et al., "Intravascular ultrasound assessment of the novel AngioSculpt scoring balloon catheter for the treatment of complex coronary lesions," J Invasive Cardiol 20(1):21-7 (Jan. 2008).

An International Search Report and a Written Opinion both dated Sep. 24, 2012, which issued during the prosecution of Applicant's PCT/IL2012/000060.

Khlif H et al., "Contribution to the Improvement of Textile Vascular Prostheses Crimping," Trends in Applied Sciences Research 6(9):1019-1027 (2011).

An International Search Report and a Written Opinion both dated Jul. 13, 2012, which issued during the prosecution of Applicant's PCT/IL2012/000083.

An International Search Report and a Written Opinion both dated Jul. 17, 2012, which issued during the prosecution of Applicant's PCT/IL2012/000095.

An International Search Report and a Written Opinion both dated Aug. 31, 2012, which issued during the prosecution of Applicant's PCT/IL2012/000148.

An International Search Report and a Written Opinion both dated Sep. 6, 2012, which issued during the prosecution of Applicant's PCT/IL2012/000190.

An International Search Report and a Written Opinion both dated Jun. 19, 2012, which issued during the prosecution of Applicant's PCT/IL2012/000241.

An International Search Report and a Written Opinion both dated Nov. 27, 2012, which issued during the prosecution of Applicant's PCT/IL2012/000300.

An International Search Report and a Written Opinion both dated Feb. 4, 2011, which issued during the prosecution of Applicant's PCT/IB2010/052861.

An International Search Report and a Written Opinion both dated Sep. 29, 2008, which issued during the prosecution of Applicant's PCT/IL08/000287.

An International Search Report and a Written Opinion both dated Mar. 11, 2009, which issued during the prosecution of Applicant's PCT/IL2007/001312.

An International Search Report and a Written Opinion both dated Jun. 30, 2009, which issued during the prosecution of Applicant's PCT/IL2008/001621.

An International Search Report and a Written Opinion both dated Nov. 5, 2010, which issued during the prosecution of Applicant's PCTIL2010000549.

An International Search Report and a Written Opinion both dated Dec. 3, 2010, which issued during the prosecution of Applicant's PCT/IL2010/000564.

An International Search Report and a Written Opinion both dated Mar. 10, 2011, which issued during the prosecution of Applicant's PCT/IL2010/000917.

An International Search Report and a Written Opinion both dated Aug. 4, 2011, which issued during the prosecution of Applicant's PCT/IL2010/000999.

An International Search Report and a Written Opinion both dated Mar. 30, 2011, which issued during the prosecution of Applicant's PCT/IL2010/001018.

An International Search Report and a Written Opinion both dated Apr. 18, 2011, which issued during the prosecution of Applicant's PCT/IL2010/001037.

An International Search Report and a Written Opinion both dated May 23, 2011, which issued during the prosecution of Applicant's PCT/IL2010/001087.

An International Search Report and a Written Opinion both dated Jun. 28, 2011, which issued during the prosecution of Applicant's PCT/IL2011/000135.

An International Search Report dated Oct. 4, 2012, which issued during the prosecution of Applicant's PCT/IL2012/000269.

An Office Action dated Apr. 27, 2011, which issued during the prosecution of U.S. Appl. No. 12/447,684.

An Office Action dated Nov. 12, 2010, which issued during the prosecution of U.S. Appl. No. 12/447,684.

An Office Action dated Mar. 24, 2011, which issued during the prosecution of U.S. Appl. No. 12/529,936.

An Office Action dated Oct. 28, 2011, which issued during the prosecution of U.S. Appl. No. 12/529,936.

An Office Action dated Jun. 19, 2012, which issued during the prosecution of U.S. Appl. No. 12/808,037.

An Office Action dated Oct. 11, 2012, which issued during the prosecution of U.S. Appl. No. 13/031,871.

European Search Report issued Feb. 24, 2014 in European Patent Application No. 12803376.8.

An Advisory Action dated Feb. 13, 2014, which issued during the prosecution of Applicant's U.S. Appl. No. 13/807,880.

An Office Action dated Feb. 28, 2014, which issued during the prosecution of Applicant's U.S. Appl. No. 13/512,778.

European Office Action issued Dec. 17, 2014 in European Patent Application No. 12803376.8.

* cited by examiner

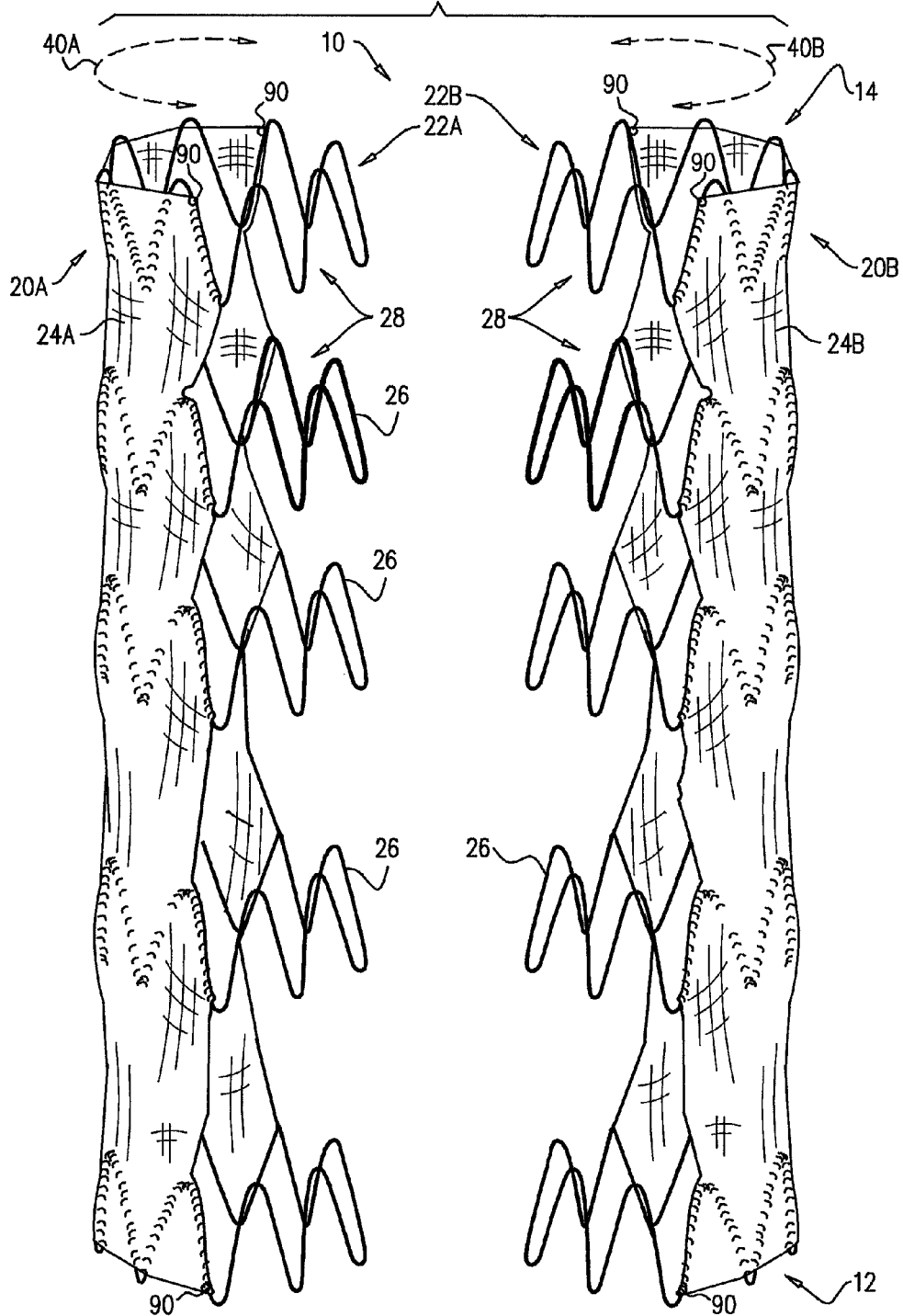

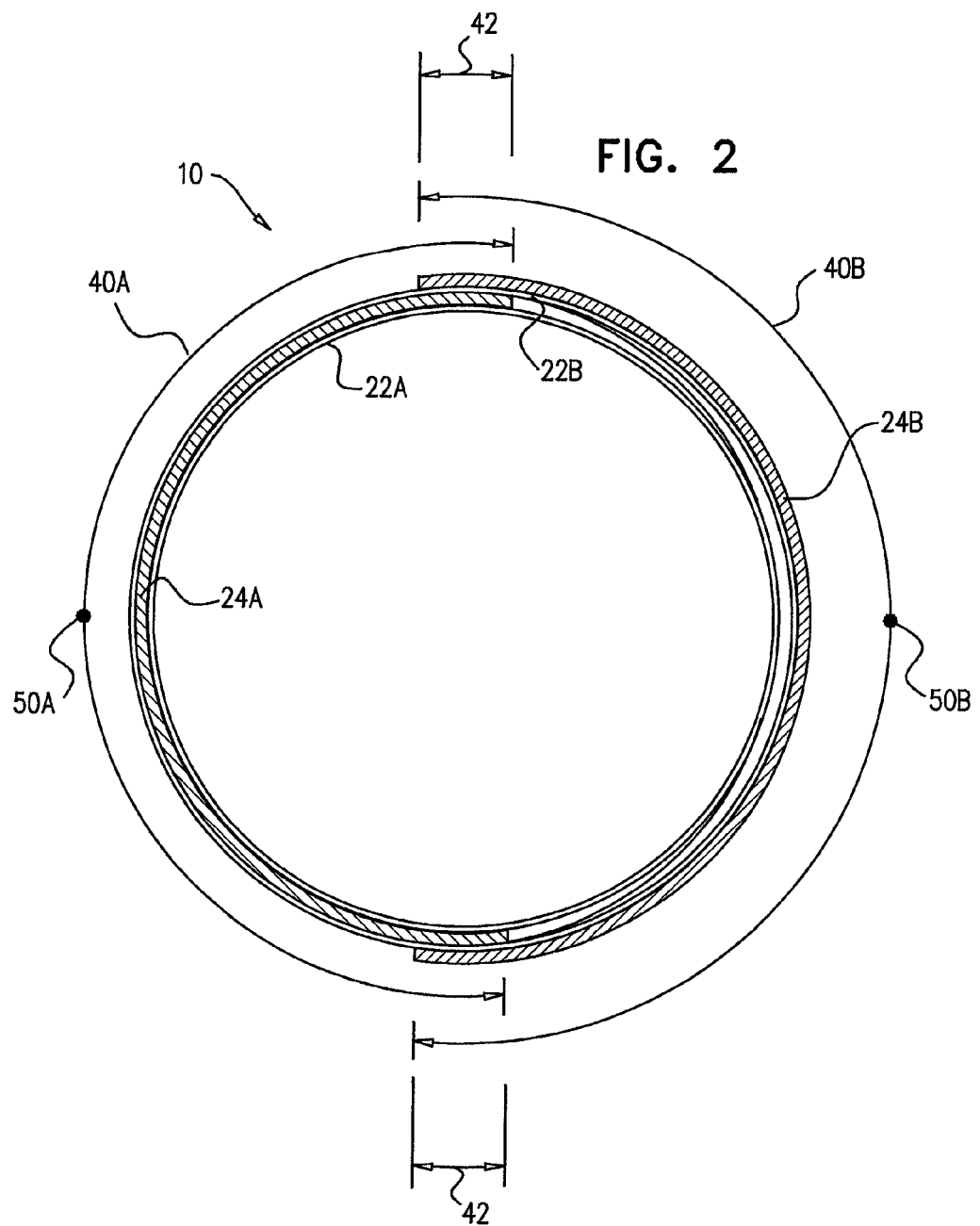

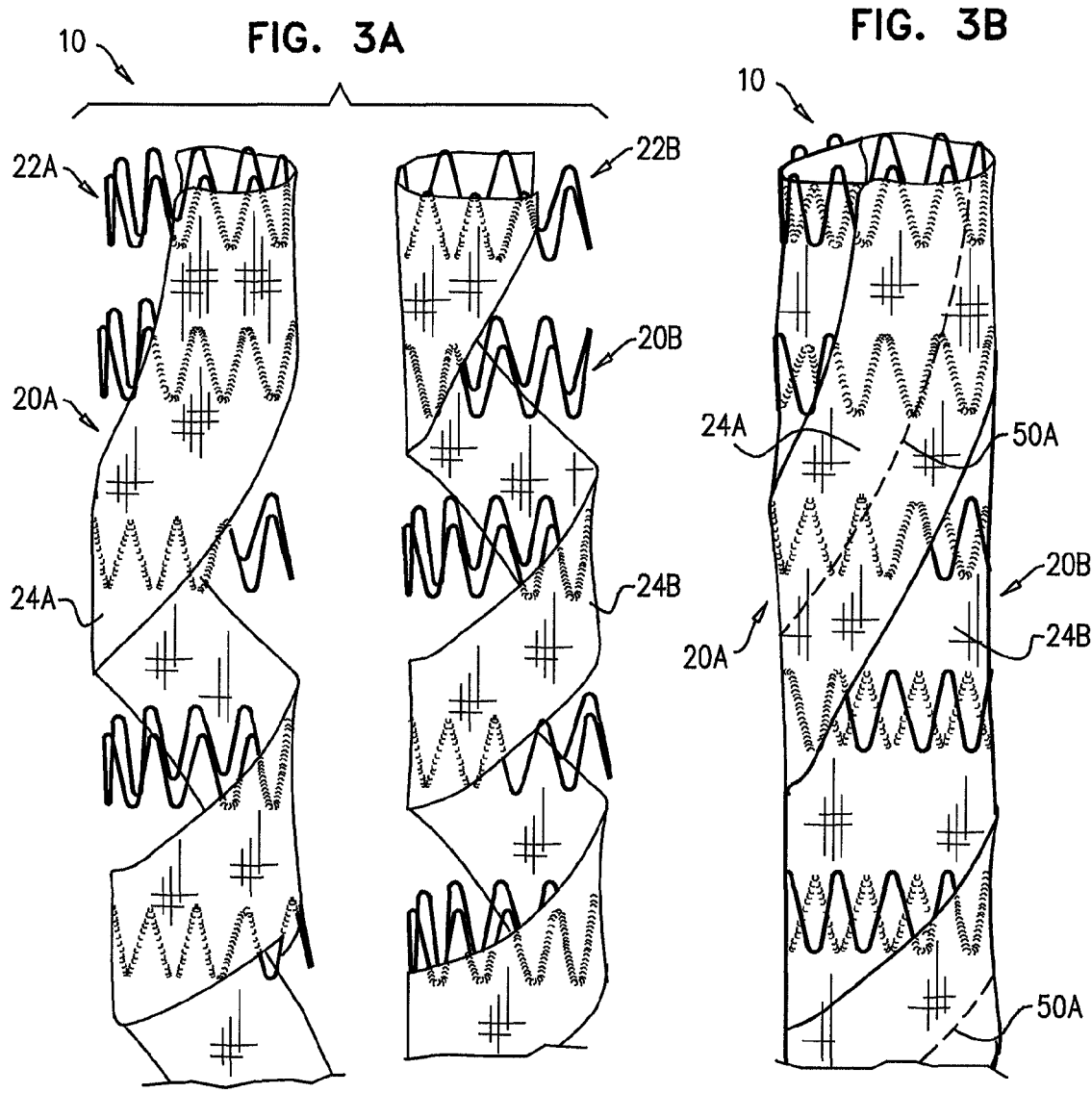

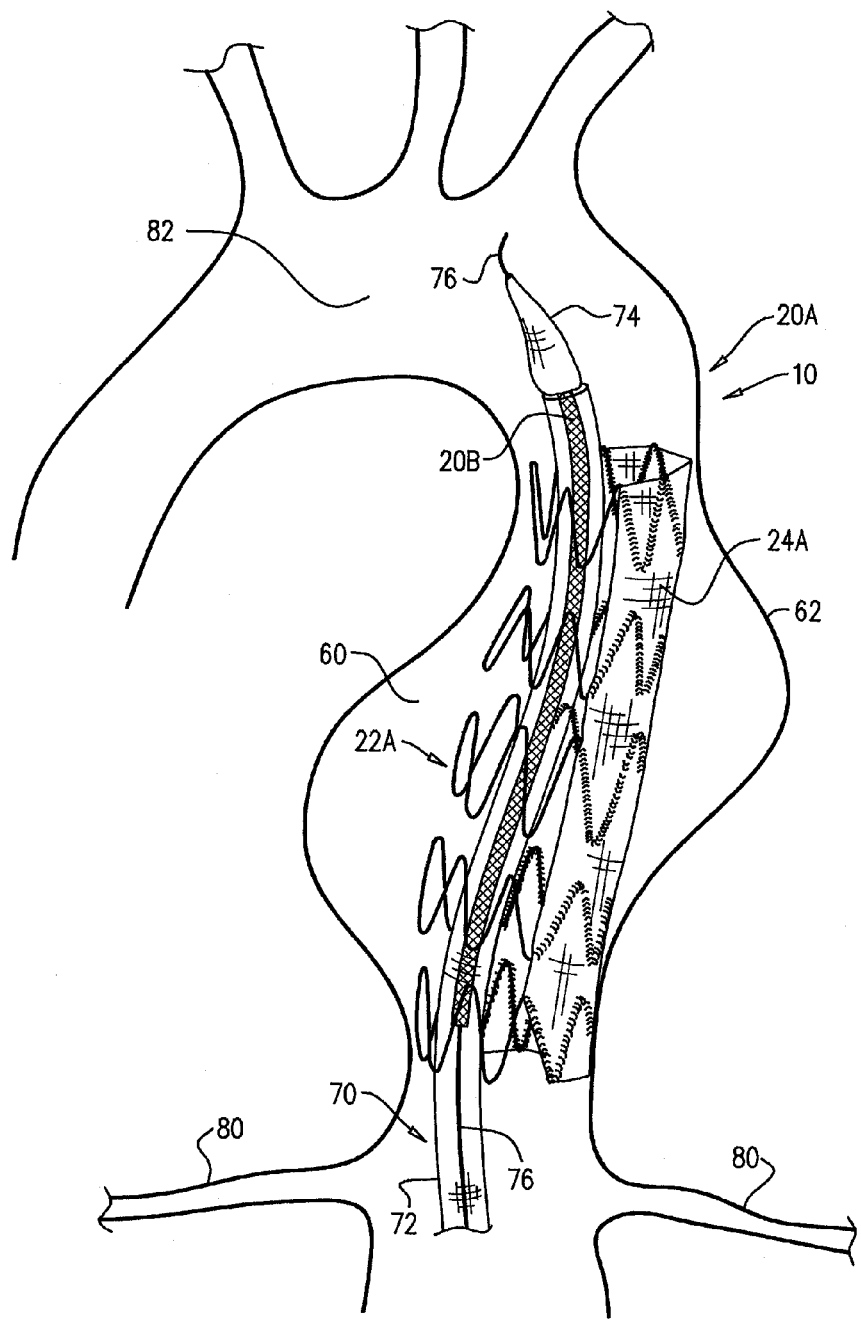

ENDOVASCULAR SYSTEM WITH CIRCUMFERENTIALLY-OVERLAPPING STENT-GRAFTS

CROSS-REFERENCE TO RELATED APPLICATIONS

The present application claims priority from U.S. patent application Ser. No. 61/499,195, filed Jun. 21, 2011, which is assigned to the assignee of the present application and is incorporated herein by reference.

FIELD OF THE APPLICATION

This present application relates generally to prostheses and surgical methods, and specifically to tubular prostheses, including endovascular grafts and stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms. A TAA may occur downstream the aortic arch, i.e., in the descending aorta. Alternatively, a TAA may occur in the aortic arch itself, where the aorta branches to supply the brachiocephalic, left carotid and subclavian arteries, or may occur in the ascending aorta.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 14 Fr or lower (3 Fr=1 millimeter), a true percutaneous approach may be used, because vascular closure devices are available for proper closure of such puncture sites. If the crossing profile at least 15-16 Fr, a vascular cut-down is usually required in advance as a preparatory step to introduction of the delivery system.

Endovascular systems for treatment of supra-renal aneurysms generally require the preparatory step of a vascular cut-down. A cut-down is the localized surgical exposure of blood vessels for accessing the subject's vasculature. For example, most surgical cut-downs used in EVAR procedures are performed in the vicinity of the pubis, exposing the iliac arteries. Surgical cut-downs have related complications and co-morbidities, including difficulty in controlling bleeding at the access site, false aneurysms, and vascular obstruction. It is therefore desirable to use a purely percutaneous approach, instead of a vascular cut-down.

Endovascular stent-grafts for treating the thoracic aorta usually require a 20-22 Fr delivery system, because of the large amount of graft material indicated by the diameter of the aorta above the level of the renal arteries (30-40 mm diameter or more in some subjects). Currently used graft materials are PET (Poly Ethylene Therephtalate) and ePTFE (expanded Poly-Tetra-Fluoro-Ethylene). The thickness and circumferential length of the graft have the most substantial effect on the crossing profile of an endovascular system. The use of thinner graft materials generally reduces long-term durability of the graft material.

SUMMARY OF APPLICATIONS

In some applications of the present invention, a multi-component endovascular stent-graft system has a body portion that comprises a plurality of stent-grafts. The stent-grafts are configured to be assembled in situ in a blood vessel of a subject to define a circumferentially-complete fluid flow path. The stent-grafts comprise respective stent members, which are shaped so as to define respective circumferentially-complete tubes when the stent-grafts are in respective radially-expanded states. The stent-grafts further comprise respective graft members that are securely fixed to the stent members, respectively. The graft members circumscribe respective circumferential arcs of the respective stent members, which circumferential arcs have respective extents that are less than entire circumferences of the respective stent members at least partially along respective axial lengths of the stent members. The graft members collectively cover an entire circumference of the body portion along the entire axial length of the body portion, when (a) the stent-grafts are nested within one another along the entire axial length of the body portion, with predefined rotational and axial relationships therebetween, and (b) the stent-grafts are in their respective radially-expanded states. Typically, in order to provide good circumferential sealing between circumferentially-adjacent stent-grafts, pairs of circumferentially-adjacent graft members have respective circumferential overlaps having respective arc extents.

Because each of the stent-grafts comprises substantially less graft and stent material than a typical single-component full-circumference stent-graft, the stent-grafts typically have relatively small crossing profiles. The stent-grafts thus can typically be deployed using catheters having a diameter of no more than 14 Fr. This generally enables the use of a true percutaneous surgical technique, without the need for a vascular cut-down. In addition, because each of the stent members defines a circumferentially-complete tube (at least one point along the length of each stent-graft), upon deployment the stent-grafts are tightly coupled to one another, and form tight blood-impervious seals with one another. Furthermore, if the stent-grafts did not define circumferentially-complete tubes, the stent-grafts might have a tendency to flatten upon deployment.

For some applications, the stent-graft system is deployed in the aorta for treating an aneurysm. During an implementation procedure, a first one of the stent-grafts is transvascularly (typically percutaneously) introduced into the aorta via one of the iliac arteries, while the stent-graft is positioned in a delivery catheter, restrained in its radially-compressed state by the catheter. After being positioned at a desired location in the aorta, the first stein-graft is deployed from the catheter, and assumes its radially-expanded state. A second one of the stent-grafts, while restrained in its radially-compressed state in a catheter, is advanced through the previously-deployed first stent-graft, until the second stent-graft is positioned at least partially (typically, entirely) within the first stent-graft, generally axially aligned with the first stent-graft. Before it is deployed from delivery catheter, the second stent-graft is properly rotationally aligned with the previously-deployed first stent-graft, such that the respective graft members of the stent-grafts will together form a circumferentially-complete fluid flow guide upon full deployment of the second stent-graft (and the other remaining stent-grafts, if any). The second stent-graft is then deployed from the catheter, thereby nesting the second stent-graft within the first stent-graft. For configurations in which the stent-graft system comprises more than two stent-grafts, the procedure described above is repeated for the additional stent-grafts, until the stein-grafts are all deployed to together form the stent-graft system. As a result, the stent-graft system has been assembled in situ to form a circumferentially complete fluid flow guide comprising all of the stent-grafts.

There is therefore provided, in accordance with an application of the present invention, apparatus including a multi-component endovascular stent-graft system, which has proximal and distal ends, and a body portion disposed along at least a part of the stent-graft system longitudinally between the proximal and distal ends, which body portion has an axial length and includes a plurality of stent-grafts, which (a) are configured to assume respective radially-compressed states for transluminal delivery, and respective radially-expanded states for intraluminal fixation, and (b) include:

respective stent members, which are shaped, when the stent-grafts are in their respective radially-expanded states, so as to define respective tubes, each of which is circumferentially-complete at least one longitudinal location therealong; and respective graft members, which respectively include one or more biologically-compatible substantially blood-impervious flexible sheets, and which are securely fixed to the stent members, respectively, such that the graft members circumscribe respective circumferential arcs of the respective stent members, which circumferential arcs have respective extents that are less than entire circumferences of the respective stent members at least partially along respective axial lengths of the stent members, when the stent-grafts are in their respective radially-expanded states, wherein the graft members collectively cover an entire circumference of the body portion along the entire axial length of the body portion, when (a) the stent-grafts are nested within one another along the entire axial length of the body portion, with predefined rotational and axial relationships therebetween, and (b) the stent-grafts are in their respective radially-expanded states.

For some applications, the graft members are securely fixed to the stent members, respectively, such that the circumferential arc extents are less than the entire circumferences of the respective stent members along at least 80% of the respective axial lengths of the stent members, when the stent-grafts are in their radially-expanded states. For some applications, the graft members are securely fixed to the stent members, respectively, such that the circumferential arc extents are less than the entire circumferences of the respective stent members along the entire respective axial lengths of the stent members, when the stent-grafts are in their radially-expanded states.

For some applications, the circumferential arcs have respective arc extents, at least one of which is between $1.1\pi$ (pi) and $1.4\pi$ (pi) radians. For some applications, each of the respective arc extents is between $1.1\pi$ (pi) and $1.4\pi$ (pi) radians. For some applications, the stent-graft system includes exactly two stent-grafts.

For some applications, the circumferential arcs have respective arc extents, at least one of which is between $0.75\pi$ (pi) and $1.1\pi$ (pi) radians. For some applications, each of the respective arc extents is between $0.75\pi$ (pi) and $1.1\pi$ (pi) radians. For some applications, the stent-graft system includes exactly three stent-grafts.

For some applications, the circumferential arcs have respective arc extents, at least one of which is between $0.6\pi$ (pi) and $0.75\pi$ (pi) radians. For some applications, each of the respective arc extents is between $0.67\pi$ (pi) and $0.752\pi$ (pi) radians. For some applications, the stent-graft system includes exactly four stent-grafts.

For some applications, pairs of circumferentially-adjacent graft members have respective circumferential overlaps having respective arc extents, each of which is at least $0.05\pi$ (pi) radians, when (a) the stent-grafts are nested within one another along the entire axial length of the body portion, with the predefined rotational and axial relationships therebetween, and (b) the stent-grafts are in their respective radially-expanded states. For some applications, each of the overlaps is at least $0.1\pi$ (pi) radians. For some applications, the circumferential arcs have respective arc extents, a sum of which is greater than $2.2\pi$ (pi) radians, when (a) the stent-grafts are nested within one another along the entire axial length of the body portion, with the predefined rotational and axial relationships therebetween, and (b) the stent-grafts are in their respective radially-expanded states. For some applications, the sum is equal to at least $2.6\pi$ (pi) radians. For some applications, the sum is equal to at least (a) $2\pi$ (pi) plus (b) a product of (i) a number of the stent-grafts and (ii) $0.1\pi$ (pi) radians.

For any of the applications described above, the circumferential arcs may have respective arc angular centers, which are positioned at respective substantially constant circumferential locations along the entire axial length of the body portion, when (a) the stent-grafts are nested within one another along the entire axial length of the body portion, with the predefined rotational and axial relationships therebetween, and (h) the stent-grafts are in their respective radially-expanded states.

For any of the applications described above, the circumferential arcs may have respective arc angular centers, which are positioned at respective circumferential locations that vary along at least a portion of the axial length of the body portion, when (a) the stent-grafts are nested within one another along the entire axial length of the body portion, with the predefined rotational and axial relationships therebetween, and (b) the stent-grafts are in their respective radially-expanded states. For some applications, the respective circumferential locations vary along the entire axial length of the body portion when (a) the stent-grafts are nested within one another along the entire axial length of the body portion, with the predefined rotational and axial relationships therebetween, and (b) the stent-grafts are in their respective radially-expanded states. For some applications, the circumferential arcs have respective arc extents, which are generally constant along the entire axial length of the body portion, when (a) the stent-grafts are nested within one another along the entire axial length of the body portion, with the predefined rotational and axial relationships therebetween, and (b) the stent-grafts are in their respective radially-expanded states.

For any of the applications described above, the circumferential arcs may have respective arc extents, which vary along the entire axial length of the body portion, when (a) the stent-grafts are nested within one another along the entire axial length of the body portion, with the predefined rotational and axial relationships therebetween, and (b) the stent-grafts are in their respective radially-expanded states.

For any of the applications described above, the stent-graft system may be shaped so as to define a side-facing fenestration, when (a) the stent-grafts are nested within one another along the entire axial length of the body portion, with the predefined rotational and axial relationships therebetween, and (b) the stent-grafts are in their respective radially-expanded states. For some applications, the side-facing fenestration is generally circular. For some applications, a perimeter of the fenestration is between 10% and 50% of a perimeter of the stent-graft system adjacent the fenestration.

For any of the applications described above, the body portion may be disposed along only part of the stent-graft system.

For any of the applications described above, the stent members may be self-expanding.

For any of the applications described above, the stent members may include a superelastic metallic alloy. Alternatively or additionally, for any of the applications described above, the stent members may include a shape memory metallic alloy. Alternatively or additionally, for any of the applications described above, the stent members may include Nitinol.

For any of the applications described above, the stent-graft system may further include a plurality of outwardly protruding fixation elements. For some applications, the fixation elements are positioned at the proximal end of the stent-graft system. For some applications, the fixation elements include barbs.

For any of the applications described above, each of the stent-grafts may further include one or more radiopaque markers.

For any of the applications described above, each of the tubes respectively defined by the stent members may be circumferentially-complete along at least three longitudinal locations thereof.

For any of the applications described above, the apparatus may further include a plurality of delivery catheters, in which the stent-grafts are respectively initially positioned in their radially-compressed states.

There is further provided, in accordance with an application of the present invention, a method including:
 (i) providing a multi-component endovascular stent-graft system, which has proximal and distal ends, and a body portion disposed along at least a part of the stent-graft system longitudinally between the proximal and distal ends, which body portion has an axial length and includes a plurality of stent-grafts, which (a) are configured to assume respective radially-compressed states for transluminal delivery, and respective radially-expanded states for intraluminal fixation, and (b) include (x) respective stent members, which are shaped so as to define respective circumferentially-complete tubes when the stent-grafts are in their respective radially-expanded states, and (y) respective graft members, which respectively include one or more biologically-compatible substantially blood-impervious flexible sheets, and which are securely fixed to the stent members, respectively, such that the graft members circumscribe respective circumferential arcs of the respective stent members, which circumferential arcs have respective extents that are less than entire circumferences of the respective stent members at least partially along respective axial lengths of the stent members, when the stent-grafts are in their respective radially-expanded states;
 (ii) transvascularly introducing a first one of the stent-grafts into a blood vessel of a human subject, while the stent-graft is restrained in its radially-compressed state;
 (iii) thereafter, deploying the first stent-graft in the blood vessel so that the first stent-graft assumes its radially-expanded state;
 (iv) thereafter, introducing another one of the stent-grafts into the blood vessel and at least partially into the first stent-graft and any of the other stent-grafts already deployed, while the another stent-graft is restrained in its radially-compressed state;
 (v) thereafter, axially and rotationally orienting the another stent-graft with the first stent-graft and any of the other stent-grafts already deployed, and deploying the another stent-graft in the blood vessel so that the another stent-graft assumes its radially-expanded state; and
 (vi) thereafter, repeating steps (iv) and (v) until all of the stent-grafts have been deployed in the blood vessel, wherein deploying the stent-grafts includes deploying the stent-grafts such that the graft members collectively cover an entire circumference of the body portion along the entire axial length of the body portion.

For some applications, deploying the stent-grafts includes deploying the stent-grafts such that pairs of circumferentially-adjacent graft members have respective circumferential overlaps having respective arc extents, each of which is at least $0.05\pi$ (pi) radians, such as at least $0.1\pi$ (pi) radians.

For some applications, providing the stent-graft system includes providing the stent-graft system in which each of the tubes respectively defined by the stent members is circumferentially-complete along an entire length thereof.

For some applications, the blood vessel is an aorta, and deploying the stent-grafts includes deploying the stent-grafts in the aorta.

For some applications, the method further includes identifying the subject as suffering from an aortic aneurysm, and deploying the stent-grafts includes deploying the stent-grafts responsively to the identifying.

The present invention will be more fully understood from the following detailed description of embodiments thereof, taken together with the drawings, in which:

BRIEF DESCRIPTION OF THE DRAWINGS

FIGS. 1A-B are schematic illustrations of a multi-component endovascular stent-graft system, disassembled and assembled, respectively, in accordance with an application of the present invention;

FIG. 2 is a schematic illustration of the stent-graft system of FIGS. 1A-B viewed from a distal end thereof, in accordance with an application of the present invention;

FIGS. 3A-B are schematic illustrations of another configuration of the multi-component endovascular stent-graft system of FIGS. 1A-B and 2, disassembled and assembled, respectively, in accordance with an application of the present invention;

FIGS. 4A-F are schematic illustrations of an exemplary method of deploying the multi-component endovascular stent-graft system of FIGS. 1A-B, 2, and/or 3 in the vicinity of an abdominal aortic aneurysm, in accordance with an application of the present invention;

DETAILED DESCRIPTION OF APPLICATIONS

Figure 1B:
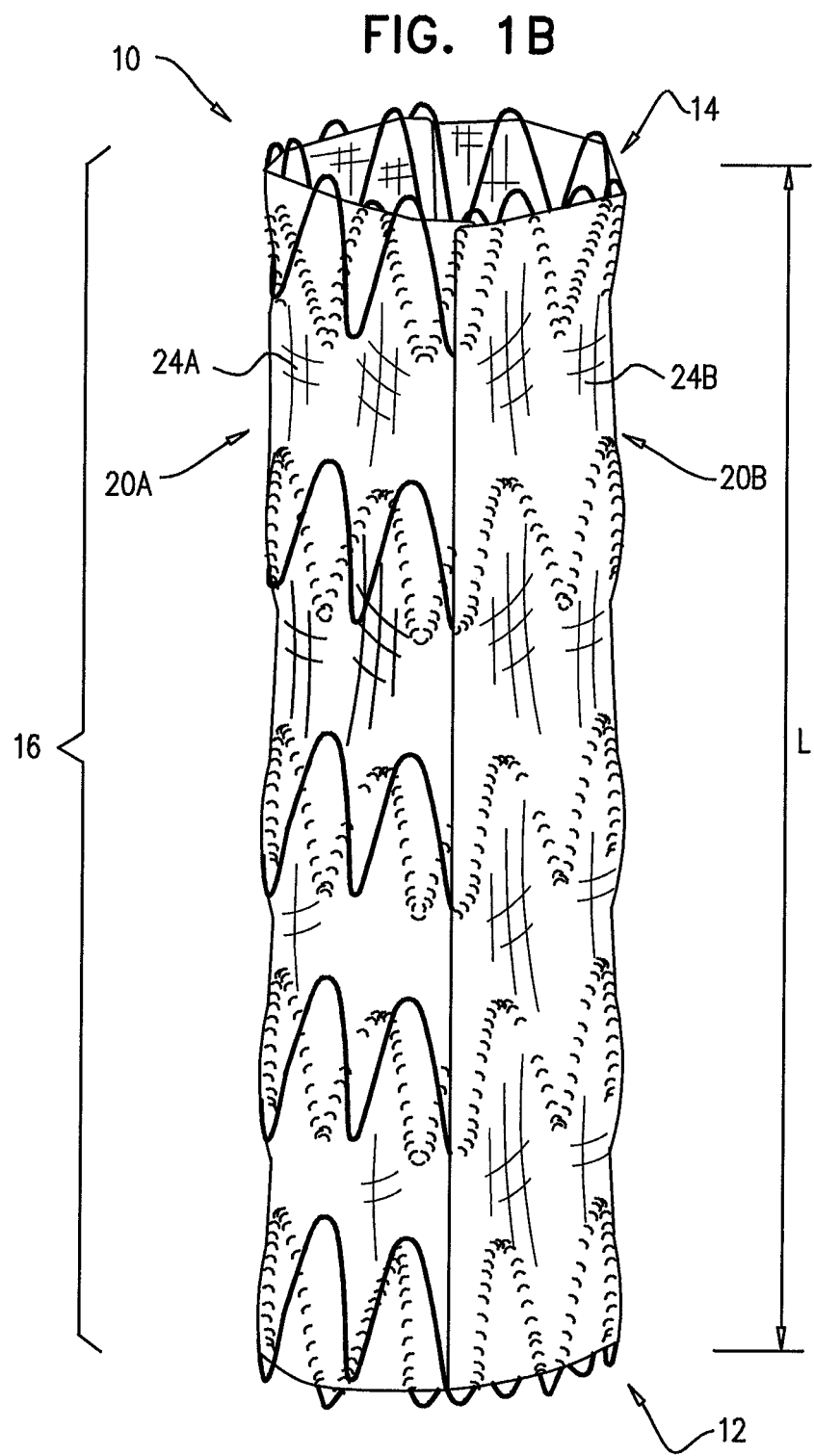

FIGS. 1A-B are schematic illustrations of a multi-component endovascular stent-graft system 10, in accordance with an application of the present invention. FIGS. 1A and 1B show the stent-graft system disassembled and assembled, respectively. Stent-graft system 10 has proximal and distal ends 12 and 14, and a body portion 16 disposed along at least a part of the stent-graft system longitudinally between proximal and distal ends 12 and 14. Body portion 16 has an axial length L (labeled in FIG. 1B). For some applications, body portion 16 extends along the entire axial length of stent-graft system 10, as shown in the figures. For other applications, the body portion extends along only part of the length of the stent-graft system, such as described hereinbelow with reference to FIG. 6.

Body portion 16 comprises a plurality of stent-grafts 20. In the exemplary configuration shown in FIGS. 1A-B, body portion 16 comprises exactly two stent-grafts 20A and 20B. Each of endovascular stent-grafts 20 is configured to initially be positioned in a delivery catheter in a radially-compressed state for transluminal delivery, such as described hereinbelow with reference to FIGS. 4A and 4C-E, and to assume a radially-expanded state upon being deployed from the delivery catheter for intraluminal fixation, such as described hereinbelow with reference to FIGS. 4B and 4F. FIGS. 1A-B show the endovascular stent-grafts in their respective radially-expanded states. For some applications, the stent-grafts are heat-set to assume the radially-expanded state.

Stent-graft system 10 is assembled in situ by nesting stent-grafts 20 within one another, as shown in FIG. 1B. The stent-grafts are typically sized such that they become tightly coupled to one another upon radial expansion, such as by radial force and/or coupling elements disposed thereupon (e.g., internally connecting barbs) or by an external device (e.g., stapler pins that connect the stent-grafts and that are applied by an independent stapling instrument). It is noted that for applications in which stent-graft system 10 comprises exactly two stent-grafts 20, one of the stent-grafts is nested within the other stent-graft. For applications in which the stent-graft system comprises exactly three stent-grafts, a first one of the stent-grafts is nested within a second one of the stent-grafts, and a third one of the stent-grafts is nested within both the first and second stent-grafts. The stent-grafts of stent-grafts systems comprising more than three stent-grafts are similarly nested within one another.

For some applications, proximal and/or distal portions of the stent-graft system extend proximally and/or distally beyond the body portion comprise anchoring elements, for example as described hereinbelow with reference to FIG. 6, and/or as described in PCT Publication WO 2010/150208, mutatis mutandis, which is incorporated herein by reference, e.g., with reference to FIGS. 3, 7A-C, 9A-B, 10A-B, 13, 15A-C, 16, 17, 18, 19, 20A-B, and/or 21A-B thereof. These proximally- and/or distally-extending portions may be components of all of stent-grafts 20, or of only a portion of stent-grafts 20, such as of only one of stent-grafts 20.

Each of stent-grafts 20 comprises a stent member 22 and a graft member 24. Stent member 22 comprises a plurality of structural stent elements (struts) 26, which, for some applications, are arranged as a plurality of circumferential bands 28. For some applications, at least some of, e.g., all of, the structural stent elements are interconnected, while for other applications, at least a portion of, e.g., all, of the structural stent elements are not interconnected. In the configuration shown in FIGS. 1A-B, circumferential bands 28 are not directly connected to one another, but instead are indirectly connected by graft member 24, to form stent-graft 20. When the stent-grafts are in their respective radially-expanded states, as shown in FIGS. 1A-B, stent members 22 are shaped so as to define respective tubes, each of which is circumferentially-complete at least one longitudinal location thereal-ong, such as along at least 2, at least 3, at least 4, at least 5, or at least 10 longitudinal locations therealong, or an entire length thereof. For some applications in which structural stent elements 26 are arranged as circumferential bands 28, the number of longitudinal locations therealong equals the number of bands 28, as shown in FIGS. 1A-B, 3A-B, and 4A-F. As used in the present application, including in the claims, a "tube" is an elongated hollow object that defines a conduit therethrough. A "tube" may have varied cross-sections therealong, and the cross-sections are not necessarily circular. For example, one or more of the cross-sections may be generally elliptical but not circular, or circular.

Typically, stent members 22 are self-expanding. For some applications, stent members 22 comprise a superelastic metallic alloy, a shape memory metallic alloy, and/or Nitinol.

Each of graft members 24 comprises one or more biologically-compatible substantially blood-impervious flexible sheets, which are securely fixed to stent member 22, either outside or within the stent member, such as by stitching, and covers either an external or an internal surface of a portion of the stent member. The flexible sheet may comprise, for example, a polymeric film material (e.g., polytetrafluoroethylene), a polymeric textile material (e.g., woven polyethylene terephthalate (PET)), natural tissue graft (e.g., saphenous vein or collagen), or a combination thereof.

Reference is still made to FIGS. 1A-B, and is additionally made to FIG. 2, which is a schematic illustration of stent-graft system 10 viewed from distal end 14, in accordance with an application of the present invention. Graft members 24 circumscribe respective circumferential arcs 40 of respective stent members 22. Circumferential arcs 40 have respective extents that are less than entire circumferences of respective stent members 22 at least partially along respective axial lengths of stent members 22, when stent-grafts 20 are in their respective radially-expanded states. In the configuration shown in FIGS. 1A-B and 2, graft member 24A circumscribes circumferential arc 40A of stent member 22A, and graft member 24B circumscribes circumferential arc 40B of stent member 22B.

As shown in FIGS. 1B and 2, graft members 24 collectively cover (either inside and/or outside) an entire circumference of body portion 16 along entire axial length L of body portion 16, when (a) stent-grafts 20 are nested within one another along entire axial length L of body portion 16, with predefined rotational and axial relationships therebetween, and (b) stent-grafts 20 are in their respective radially-expanded states. As a result, graft members 24 collectively define a fluid flow guide along entire axial length L of body portion 16, in order to define a fluid flow path through the body portion.

Typically, graft members 24 are securely fixed to stent members 22, respectively, such that the circumferential arc extents are less than the entire circumferences of the respective stent members along at least 80% of the respective axial lengths of stent members 22, such as along at least 90%, or the entire respective axial lengths, of the stent members, when the stent-grafts are in their radially-expanded states. As a result, when the graft members are radially-compressed for delivery, the crossing profiles of the graft members are less than they would be if the graft members extended around the entire circumferences of the stent members.

For some applications, such as in which stent-graft system 10 comprises exactly two stent-grafts 20, circumferential arcs 40 have respective arc extents, at least one of which is between $1.1\pi$ (pi) and $1.4\pi$ (pi) radians. Optionally, each (i.e., all) of the respective arc extents is between $1.1\pi$ (pi) and $1.4\pi$ (pi) radians. For some applications, such as in which stent-graft system 10 comprises exactly three stent-grafts 20, circumferential arcs 40 have respective arc extents, at least one of which is between $0.75\pi$ (pi) and $1.1\pi$ (pi) radians. Optionally, each (i.e., all) of the respective arc extents is between 0.75π (pi) and 1.1π (pi) radians. For some applications, such as in which stent-graft system 10 comprises exactly four stent-grafts 20, circumferential arcs 40 have respective arc extents, at least one of which is between 0.6π (pi) and 0.75π (pi) radians. Optionally, each (i.e., all) of the respective arc extents is between 0.6π (pi) and 0.75π (pi) radians.

Typically, in order to provide good circumferential sealing between circumferentially-adjacent stent-grafts 20, pairs of circumferentially-adjacent graft members 22 have respective circumferential overlaps 42 having respective arc extents, when (a) stent-grafts 20 are nested within one another along entire axial length L of body portion 16, with the predefined rotational and axial relationships therebetween, and (b) stent-grafts 20 are in their respective radially-expanded states. Typically, each of the arc extents is at least 0.05π (pi) radians, such as at least 0.1π (pi) radians.

For some applications, circumferential arcs 40 have respective arc extents, a sum of which is greater than 2.2π (pi) radians, such as at least 2.6π (pi) radians, when (a) stent-grafts 20 are nested within one another along entire axial length L of the body portion 16, with the predefined rotational and axial relationships therebetween, and (b) stent-grafts 20 are in their respective radially-expanded states. Optionally, the sum is equal at least (a) 2π (pi) plus (b) a product of (i) a number of stent-grafts 20 and (ii) 0.1π (pi) radians.

For some applications, such as shown in FIGS. 1A-B and 2, circumferential arcs 40 have respective arc angular centers 50, which are positioned at respective substantially constant circumferential locations along the entire axial length of body portion 16, when (a) stent-grafts 20 are nested within one another along entire axial length L of body portion 16, with the predefined rotational and axial relationships therebetween, and (b) stent-grafts 20 are in their respective radially-expanded states. In other words, the circumferential centers of graft members 24 do not vary along the length of the body portion, for example, do not form a helical shape around the body portion.

Alternatively or additionally, for some applications, circumferential arcs 40 have respective arc extents, which are generally constant along entire axial length L of the body portion 16, when (a) stent-grafts 20 are nested within one another along entire axial length L of body portion 16, with the predefined rotational and axial relationships therebetween, and (b) stent-grafts 20 are in their respective radially-expanded states. Alternatively, the arc extents vary along at least a portion (e.g., the entire) axial length L of body portion 16.

Reference is now made to FIGS. 3A-B, which are schematic illustrations of another configuration of multi-component endovascular stent-graft system 10, in accordance with an application of the present invention. FIGS. 3A and 3B show the stent-graft system disassembled and assembled, respectively. This configuration is generally similar to the configuration described hereinabove with reference to FIGS. 1A-B and 2, except as follows. In this configuration, respective arc angular centers 50 of circumferential arcs 40 are positioned at respective circumferential locations that vary along at least a portion of axial length L of body portion 16, when (a) stent-grafts 20 are nested within one another along entire axial length L of body portion 16, with the predefined rotational and axial relationships therebetween, and (b) stent-grafts 20 are in their respective radially-expanded states. For example, as shown in FIGS. 3A-B, arc angular centers 50 may form a helical shape around body portion 16 (arc angular center 50A of circumferential arc 40A of stent member 22 is labeled in FIG. 3B). Optionally, the respective circumferential locations vary along the entire axial length of body portion 16.

Alternatively or additionally, for some applications, circumferential arcs 40 have respective arc extents, which are generally constant along entire axial length L of the body portion 16, when (a) stent-grafts 20 are nested within one another along entire axial length L of body portion 16, with the predefined rotational and axial relationships therebetween, and (b) stent-grafts 20 are in their respective radially-expanded states. Alternatively, the arc extents vary along at least a portion (e.g., the entire) axial length L of body portion 16.

Figure 4A:
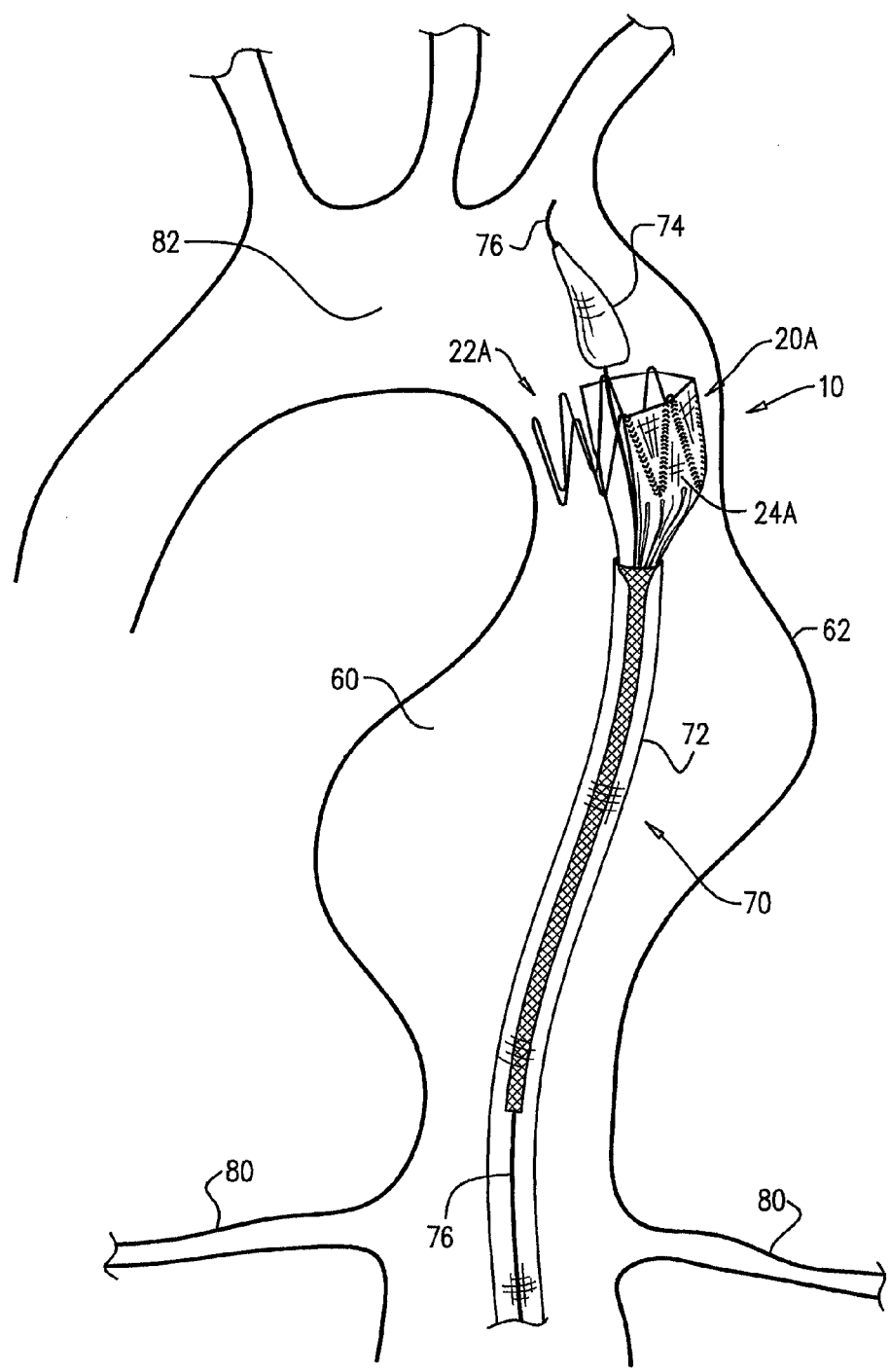

Reference is now made to FIGS. 4A-F, which are schematic illustrations of an exemplary method of deploying multi-component endovascular stent-graft system 10 in the vicinity of an supra-renal abdominal aortic aneurysm 60 of an abdominal aorta 62, using an endovascular stent-graft delivery tool 70, in accordance with an application of the present invention. As shown in FIG. 4A, delivery tool 70 typically comprises a delivery catheter 72, a distal tip 74, and a guidewire 76. During an implementation procedure, a first one of stent-grafts 20 (e.g., stent-graft 20A) is transvascularly (typically percutaneously) introduced into aorta 62 via one of the iliac arteries, while stent-graft 20A is positioned in delivery catheter 72, restrained in its radially-compressed state by the catheter. In this exemplary deployment, delivery catheter 72 and distal tip 74 are advanced over guidewire 76 until the distal tip is positioned slightly below aortic arch 82, and the lower end of the stent-graft is positioned above renal arteries 80.

Figure 4B:
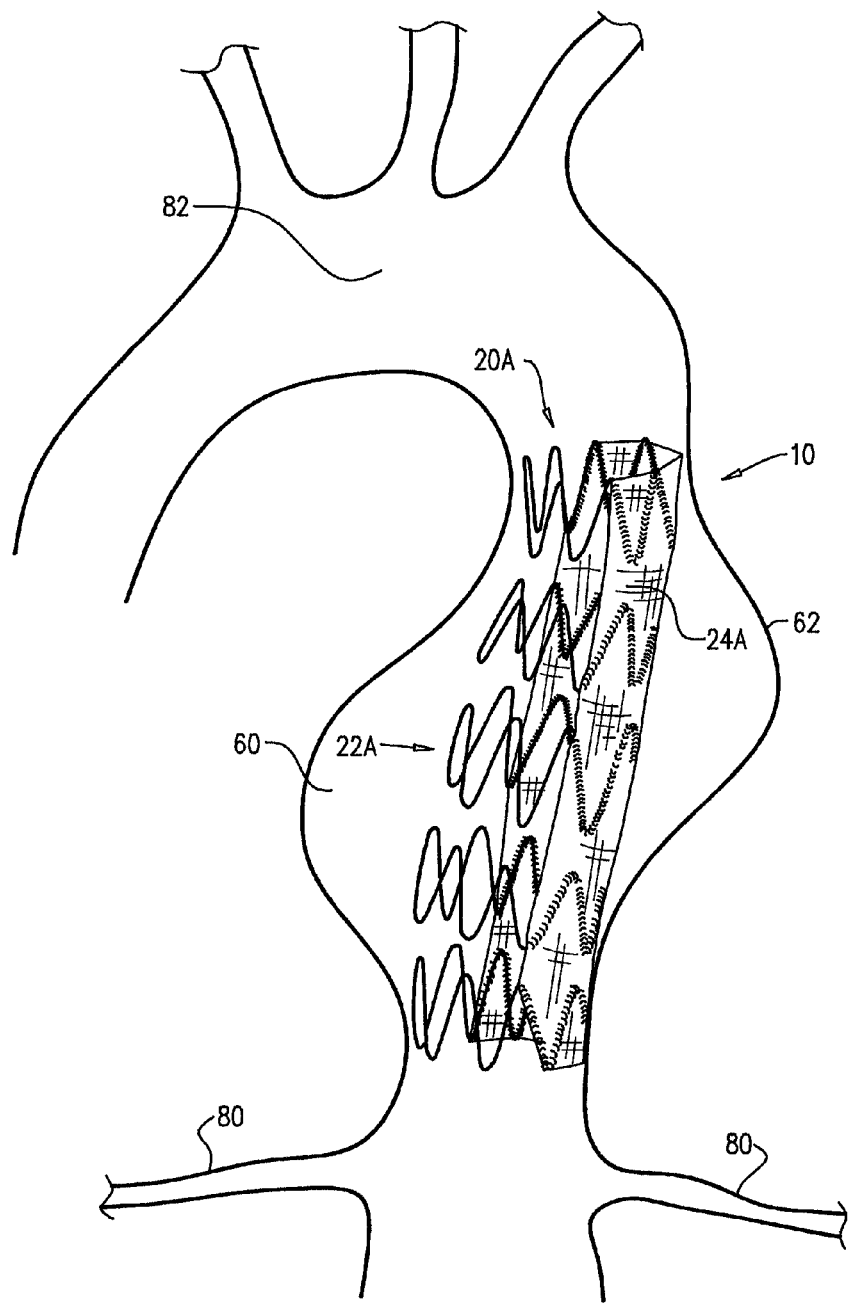

FIG. 4A shows stent-graft 20A in an early stage of release from delivery catheter 72, and FIG. 4B shows stent-graft 20A in its fully deployed, radially-expanded state, after delivery catheter 72 has been withdrawn.

As shown in FIG. 4C, a second one of stent-grafts 20 (e.g., stent-graft 20B) is positioned in a delivery catheter (either the same delivery catheter 72 used to deploy the first stent-graft, or an additional delivery catheter), restrained in the stent-graft's radially-compressed state by the catheter. Delivery catheter 72, distal tip 74, and guidewire 76 are advanced through the previously-deployed first stent-graft (stent-graft 20A), until stent-graft 20B is positioned at least partially (e.g., entirely) within stent-graft 20A, generally axially aligned with stent-graft 20A.

Figure 4D:
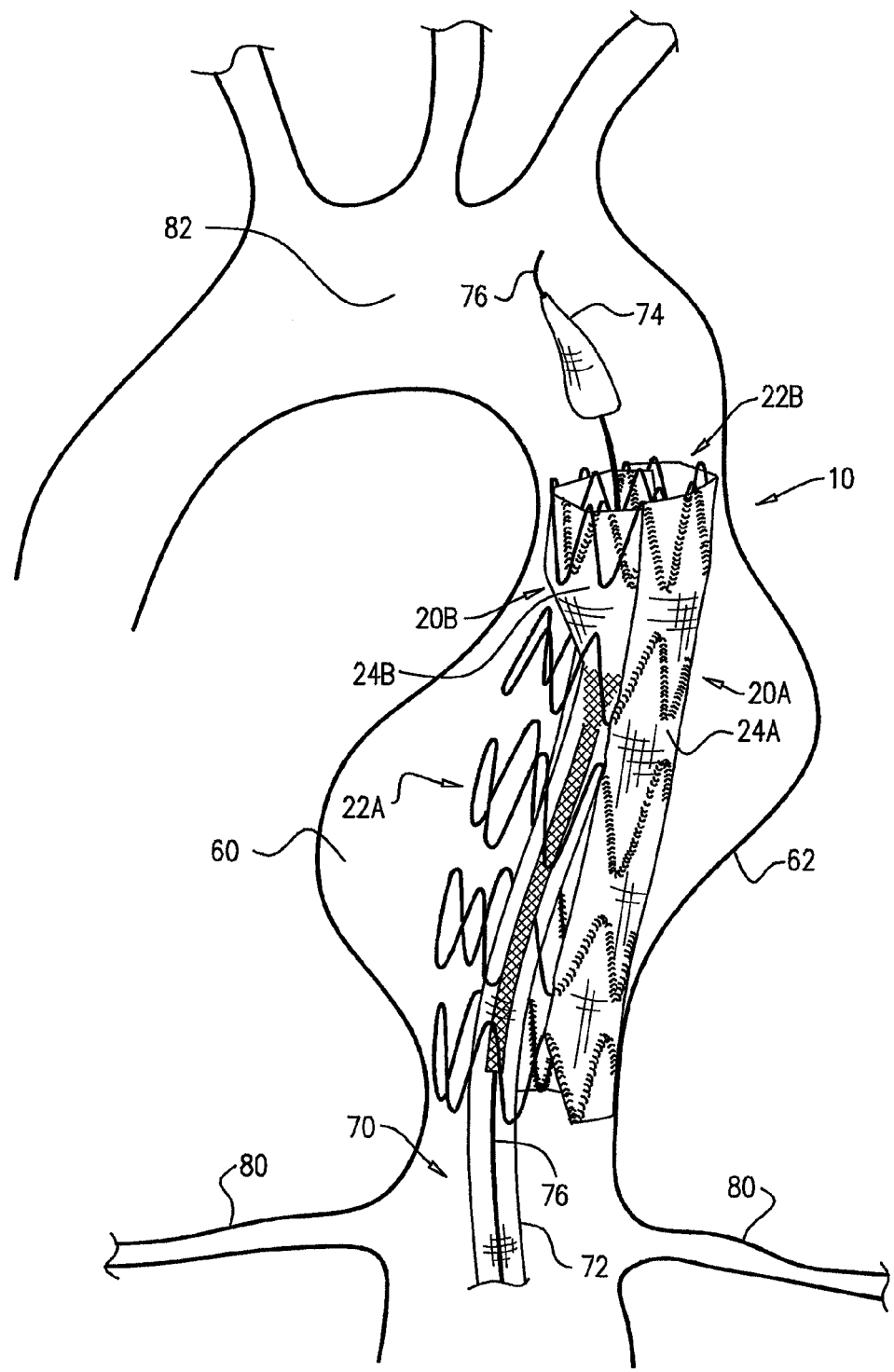

Before it is deployed from delivery catheter 72, stent-graft 20B is properly rotationally aligned with previously-deployed stent-graft 20A, such that graft members 24A and 24B (and the other remaining stent-grafts 20, if any, as described below) will together form a circumferentially-complete fluid flow guide upon full deployment of stent-graft 20B (and the other remaining stent-grafts 20, if any, as described below). FIG. 4D shows stent-graft 20B in an early stage of release from delivery catheter 72.

Figure 4E:
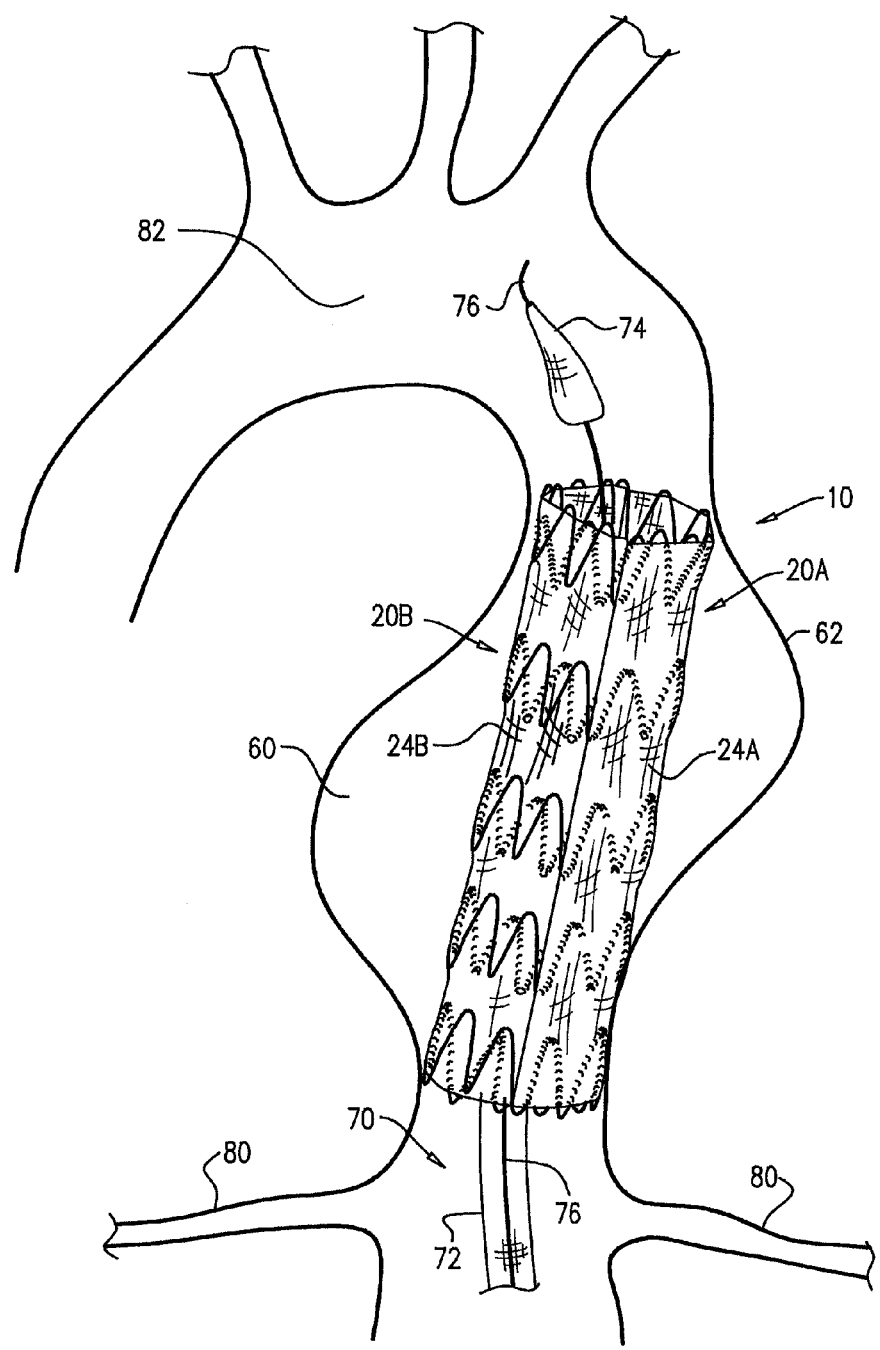
Figure 4F:
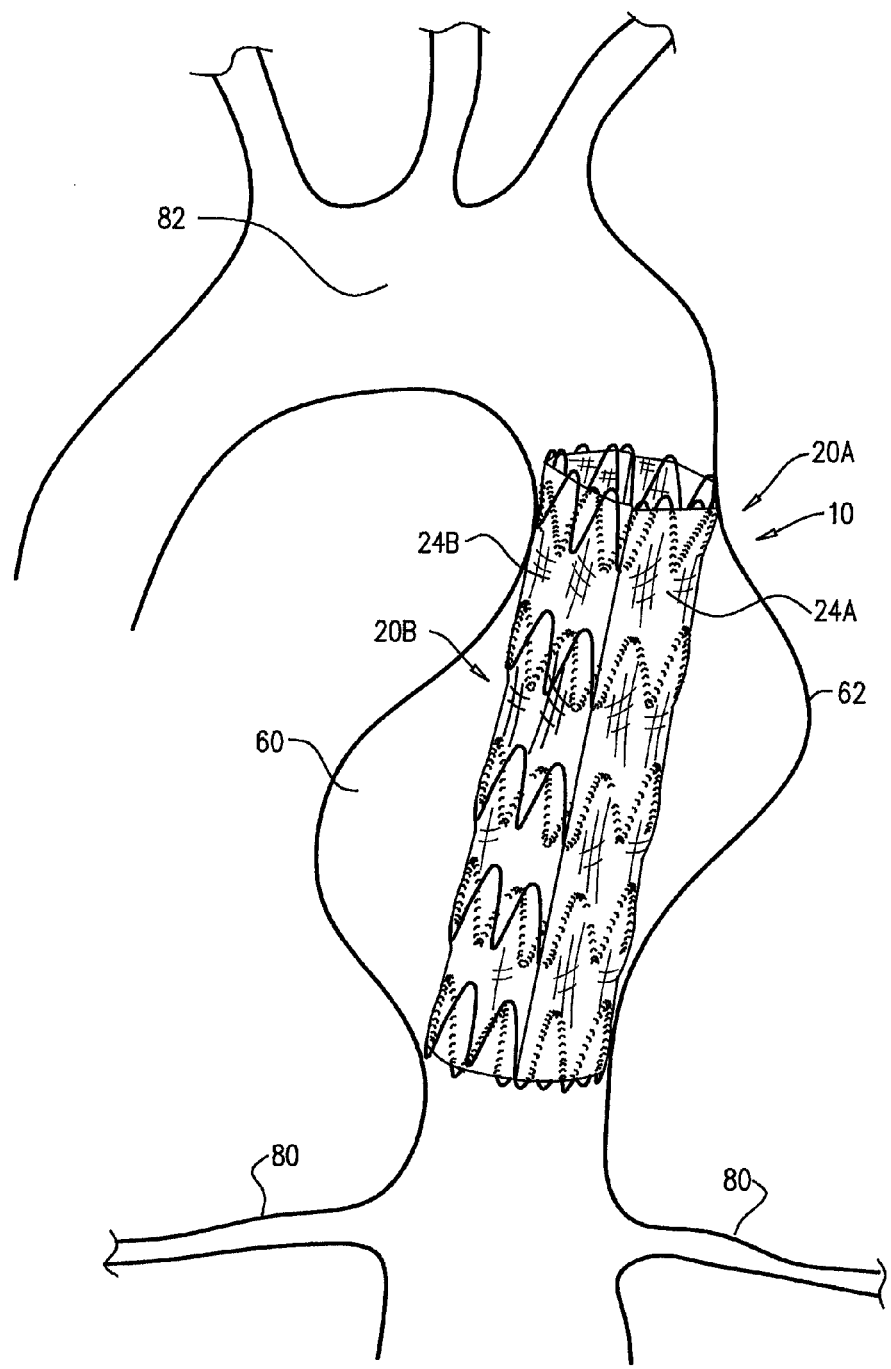

FIG. 4E shows stent-graft 20B in its fully deployed radially-expanded state, after the catheter has been withdrawn from the stent-graft. As can be seen, stent-graft 20B is nested within stent-graft 20A, and stent-graft system 10 has been assembled in situ to form a circumferentially complete fluid flow guide comprising first and second stent-grafts 20A and 20B. FIG. 4F shows the stent-graft system 10 fully implanted upon the withdrawal of delivery tool 70 and completion of the implantation procedure.

For configurations in which stent-graft system 10 comprises more than two stent-grafts 20, the procedure described above for deploying stent-grafts 20A and 20B is repeated for the additional stent-grafts, until the stent-grafts are all deployed to together form stent-graft system 10. Each of the subsequently-deployed stent-grafts is positioned at least partially within all of the already-deployed stent-grafts.

Reference is again made to FIG. 1. For some applications, each of stent-grafts 20 further comprises one or more radiopaque markers 90. The radiopaque markers may help the surgeon properly axially and/or rotationally align the stent-grafts with one another, such as described hereinabove with reference to FIG. 4D. For some applications, the radiopaque markers are disposed near edges of the graft members.

Figure 5:
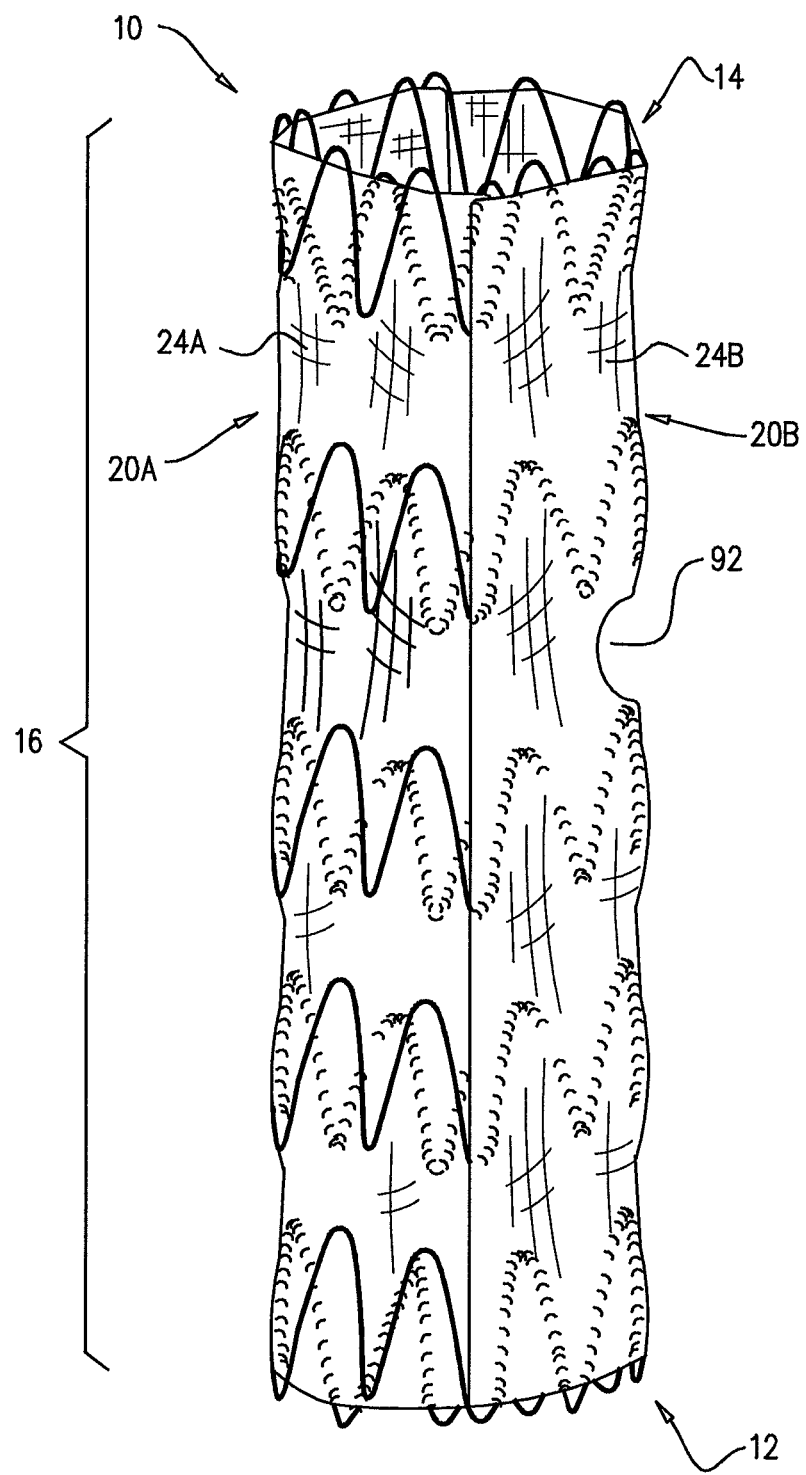
FIG. 5 is a schematic illustration of another configuration of the stent-graft system of FIGS. 1A-B, in accordance with an application of the present invention.

Reference is made to FIG. 5, which is a schematic illustration of another configuration of stent-graft system 10, in accordance with an application of the present invention. In this configuration, stent-graft system 10 is shaped so as to define a side-facing fenestration 92, when (a) stent-grafts 20 are nested within one another along entire axial length L of body portion 16, with the predefined rotational and axial relationships therebetween, and (b) stent-grafts 20 are in their respective radially-expanded states. For some applications, the side-facing fenestration is generally elliptical, such as generally circular. For some applications, a perimeter of the fenestration is between 10% and 50% of a perimeter of stent-graft system 10 adjacent the fenestration. This fenestrated configuration may be used in combination with any of the configurations described herein.

Figure 6:
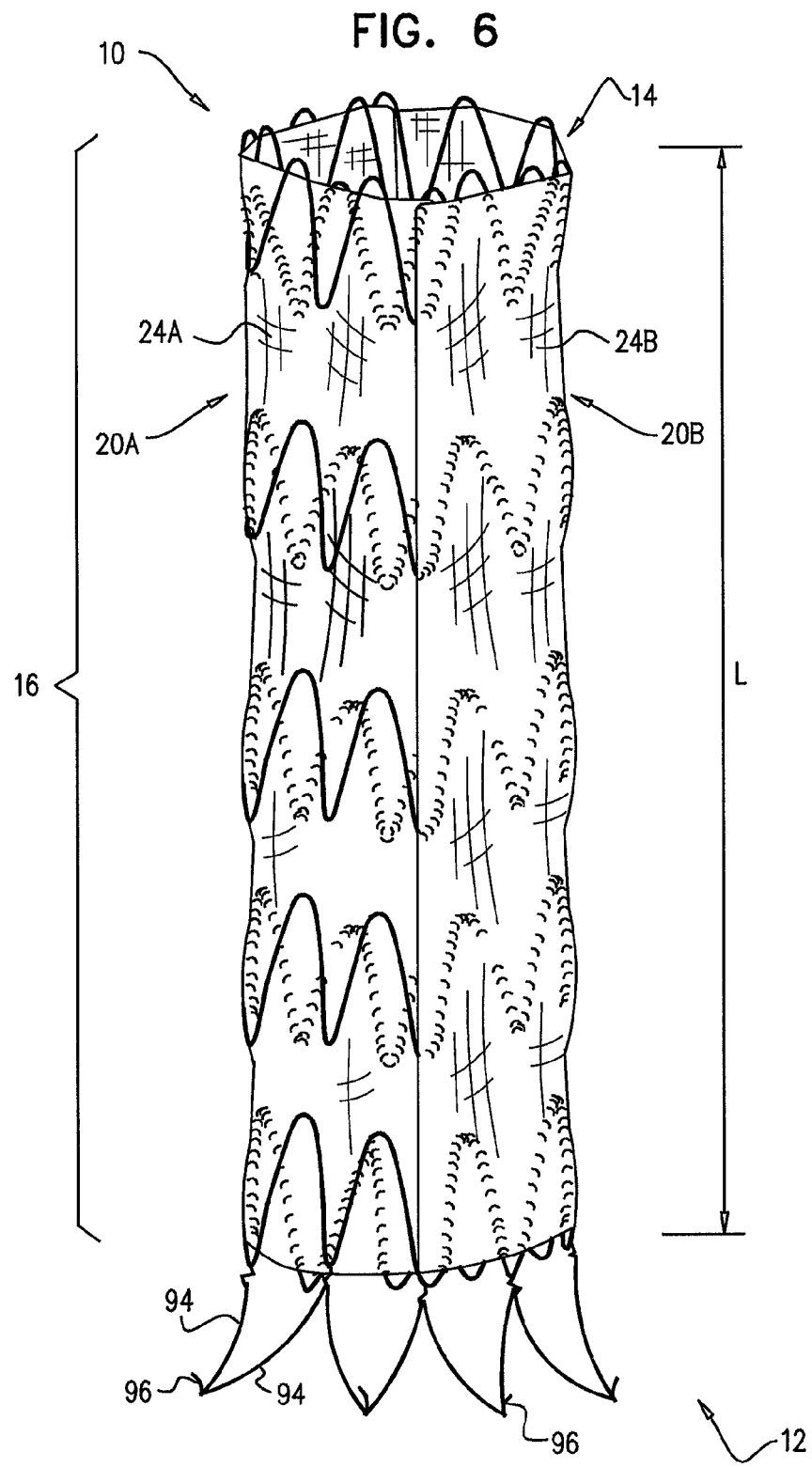
FIG. 6 is a schematic illustration of yet another configuration of the stent-graft system of FIGS. 1A-B, in accordance with an application of the present invention.

Reference is made to FIG. 6, which is a schematic illustration of yet another configuration of stent-graft system 10, in accordance with an application of the present invention. This configuration may be used in combination with any of the configurations described herein. In this configuration, stent-graft system 10 further comprises a plurality of outwardly protruding fixation elements 94. For example, fixation elements 94 may be positioned at proximal end 12 of stent-graft system 10, as shown; alternatively or additionally, fixation elements 94 may be positioned at distal end 14 of stent-graft system 10 (not shown). For some applications, fixation elements 94 comprise barbs 96. It is noted that, by way of example, fixation elements 94 shown in FIG. 6 are positioned proximally beyond body portion 16, and thus are not included in axial length L; thus, in this configuration, body portion 16 extends along only part of the length of stent-graft system 10. For some applications, all of stent-grafts 20 comprise the fixation elements, while for other applications, only a portion of the stent-grafts, such as exactly one of the stent-grafts, comprise the fixation elements. For some applications, fixation elements (e.g., barbs) are configured as shown in FIGS. 1, 2, 3, 5A-B, 7A, 7B, 7C, 9A-D, 10A, 10B, 13, 15A-C, 16, 17, 18, 19, 20, and/or 20A-B of the above-mentioned '208 publication, mutatis mutandis.

Stent-graft system 10 may be deployed alone, or as a component of a larger stent-graft system comprising additional stent-grafts, for example as described with reference to FIGS. 4E and/or 21B of the '208 publication, mutatis mutandis, or in PCT Publication WO 08/107885, mutatis mutandis, which is incorporated herein by reference. For some applications, stent-graft system 10 defines a single lumen, while for other applications, the stent-graft system 10 defines a plurality of lumen, e.g., is bifurcated, such as described with reference to FIG. 3 of the above-mentioned '208 publication, mutatis mutandis.

Although the endovascular stent-graft system is generally described herein as being deployed via an iliac artery and the aorto-iliac bifurcation, for some applications, the prostheses are instead deployed via a subclavian artery. Furthermore, although the endovascular stent-graft system is generally described herein as being deployed in the aorta, the system may also be deployed in another blood vessel, such as another artery, e.g., an aneurysmatic artery, such as an aneurysmatic iliac artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, which published as PCT Publication WO 2011/095979

US Application 13/031,871, filed Feb. 22, 2011, which published as US Patent Application Publication 2011/0208289

U.S. Provisional Application 61/496,613, filed Jun. 14, 2011

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a multi-component endovascular stent-graft system, which has proximal and distal ends, and a body portion disposed along at least a part of the stent-graft system longitudinally between the proximal and distal ends, which body portion has an axial length and comprises a plurality of stent-grafts, which (a) are configured to assume respective radially-compressed states for transluminal delivery, and respective radially-expanded states for intraluminal fixation, and (b) comprise:

respective stent members, which are shaped, when the stent-grafts are in their respective radially-expanded states, so as to define respective tubes, each of which is circumferentially-complete at least one longitudinal location therealong; and respective graft members, which respectively comprise one or more biologically-compatible substantially blood-impervious flexible sheets, and which are securely fixed to the stent members, respectively, such that the graft members circumscribe respective circumferential arcs of the respective stent members, which circumferential arcs have respective extents that are less than entire circumferences of the respective stent members at least partially along respective axial lengths of the stent members, when the stent-grafts are in their respective radially-expanded states wherein the graft members collectively cover an entire circumference of the body portion and define a circumferentially-closed volume along the entire axial length of the body portion, when (a) the stent-grafts are nested within one another along the entire axial length of the body portion, with predefined rotational and axial relationships therebetween, and (b) the stent-grafts are in their respective radially-expanded states.

2. The apparatus according to claim 1, wherein the graft members are securely fixed to the stent members, respectively, such that the circumferential arc extents are less than the entire circumferences of the respective stent members along at least 80% of the respective axial lengths of the stent members, when the stent-grafts are in their radially-expanded states.

3. The apparatus according to claim 2, wherein the graft members are securely fixed to the stent members, respectively, such that the circumferential arc extents are less than the entire circumferences of the respective stent members along the entire respective axial lengths of the stent members, when the stent-grafts are in their radially-expanded states.

4. The apparatus according to claim 1, wherein at least one of the respective arc extents is between $1.1\pi$ (pi) and $1.4\pi$ (pi) radians.

5. The apparatus according to claim 1, wherein at least one of the respective arc extents is between $0.75\pi$ (pi) and $1.1\pi$ (pi) radians.

6. The apparatus according to claim 1, wherein at least one of the respective arc extents is between $0.6\pi$ (pi) and $0.75\pi$ (pi) radians.

7. The apparatus according to claim 1, wherein pairs of circumferentially-adjacent graft members have respective circumferential overlaps having respective arc extents, each of which is at least $0.05\pi$ (pi) radians, when (a) the stent-grafts are nested within one another along the entire axial length of the body portion, with the predefined rotational and axial relationships therebetween, and (b) the stent-grafts are in their respective radially-expanded states.

8. The apparatus according to claim 7, wherein each of the overlaps is at least $0.1\pi$ (pi) radians.

9. The apparatus according to claim 7, wherein a sum of the respective arc extents is greater than $2.2\pi$ (pi) radians, when (a) the stent-grafts are nested within one another along the entire axial length of the body portion, with the predefined rotational and axial relationships therebetween, and (b) the stent-grafts are in their respective radially-expanded states.

10. The apparatus according to claim 9, wherein the sum is equal to at least $2.6\pi$ (pi) radians.

11. The apparatus according to claim 9, wherein the sum is equal at least (a) $2\pi$ (pi) plus (b) a product of (i) a number of the stent-grafts and (ii) $0.1\pi$ (pi) radians.

12. The apparatus according to claim 1, wherein the circumferential arcs have respective arc angular centers, which are positioned at respective circumferential locations that vary along at least a portion of the axial length of the body portion, when (a) the stent-grafts are nested within one another along the entire axial length of the body portion, with the predefined rotational and axial relationships therebetween, and (b) the stent-grafts are in their respective radially-expanded states.

13. The apparatus according to claim 1, wherein the stent-graft system is shaped so as to define a side-facing fenestration, when (a) the stent-grafts are nested within one another along the entire axial length of the body portion, with the predefined rotational and axial relationships therebetween, and (b) the stent-grafts are in their respective radially-expanded states.

14. The apparatus according to claim 12, wherein the respective circumferential locations vary along the entire axial length of the body portion when (a) the stent-grafts are nested within one another along the entire axial length of the body portion, with the predefined rotational and axial relationships therebetween, and (b) the stent-grafts are in their respective radially-expanded states.

15. The apparatus according to claim 12, wherein the respective arc extents are generally constant along the entire axial length of the body portion, when (a) the stent-grafts are nested within one another along the entire axial length of the body portion, with the predefined rotational and axial relationships therebetween, and (b) the stent-grafts are in their respective radially-expanded states.

16. The apparatus according to claim 13, wherein the side-facing fenestration is generally circular.

17. The apparatus according to claim 16, wherein a perimeter of the fenestration is between 10% and 50% of a perimeter of the stent-graft system adjacent the fenestration.

18. A method comprising:
(i) providing a multi-component endovascular stent-graft system, which has proximal and distal ends, and a body portion disposed along at least a part of the stent-graft system longitudinally between the proximal and distal ends, which body portion has an axial length and comprises a plurality of stent-grafts, which (a) are configured to assume respective radially-compressed states for transluminal delivery, and respective radially-expanded states for intraluminal fixation, and (b) include (x) respective stent members, which are shaped, when the stent-grafts are in their respective radially-expanded states, so as to define respective tubes, each of which is circumferentially-complete at least one longitudinal location therealong, and (y) respective graft members, which respectively comprise one or more biologically-compatible substantially blood-impervious flexible sheets, and which are securely fixed to the stent members, respectively, such that the graft members circumscribe respective circumferential arcs of the respective stent members, which circumferential arcs have respective extents that are less than entire circumferences of the respective stent members at least partially along respective axial lengths of the stent members, when the stent-grafts are in their respective radially-expanded states;
(ii) transvascularly introducing a first one of the stent-grafts into a blood vessel of a human subject, while the stent-graft is restrained in its radially-compressed state;
(iii) thereafter, deploying the first stent-graft in the blood vessel so that the first stent-graft assumes its radially-expanded state;
(iv) thereafter, introducing another one of the stent-grafts into the blood vessel and at least partially into the first stent-graft and any of the other stent-grafts already deployed, while the another stent-graft is restrained in its radially-compressed state;

(v) thereafter, axially and rotationally orienting the another stent-graft with the first stent-graft and any of the other stent-grafts already deployed, and deploying the another stent-graft in the blood vessel so that the another stent-graft assumes its radially-expanded state; and (vi) thereafter, repeating steps (iv) and (v) until all of the stent-grafts have been deployed in the blood vessel wherein deploying the stent-grafts comprises deploying the stent-grafts such that the graft members collectively cover an entire circumference of the body portion and define a circumferentially-closed volume along the entire axial length of the body portion.

19. The method according to claim 18, wherein deploying the stent-grafts comprises deploying the stent-grafts such that pairs of circumferentially-adjacent graft members have respective circumferential overlaps having respective arc extents, each of which is at least $0.05\pi$ (pi) radians.

20. The method according to claim 19, wherein each of the overlaps is at least $0.1\pi$ (pi) radians.

21. The method according to claim 18, wherein providing the stent-graft system comprises providing the stent-graft system in which each of the tubes respectively defined by the stent members is circumferentially-complete along at least three longitudinal locations thereof.

22. The method according to claim 18, wherein the blood vessel is an aorta, and wherein deploying the stent-grafts comprises deploying the stent-grafts in the aorta.

23. The method according to claim 22, further comprising identifying the subject as suffering from an aortic aneurysm, and wherein deploying the stent-grafts comprises deploying the stent-grafts responsively to the identifying.

24. The apparatus according to claim 1, wherein the circumferential arcs have respective arc angular centers, which are positioned at respective substantially constant circumferential locations along the entire axial length of the body portion, when (a) the stent-grafts are nested within one another along the entire axial length of the body portion, with the predefined rotational and axial relationships therebetween, and (b) the stent-grafts are in their respective radially-expanded states.

25. The apparatus according to claim 1, wherein the respective arc extents vary along the entire axial length of the body portion, when (a) the stent-grafts are nested within one another along the entire axial length of the body portion, with the predefined rotational and axial relationships therebetween, and (b) the stent-grafts are in their respective radially-expanded states.

26. The apparatus according to claim 1, wherein the body portion is disposed along only part of the stent-graft system.

27. The apparatus according to claim 1, wherein the stent-graft system further comprises a plurality of outwardly protruding fixation elements.

28. The apparatus according to claim 1, wherein each of the tubes respectively defined by the stent members is circumferentially-complete along at least three longitudinal locations thereof.

29. The apparatus according to claim 1, further comprising a plurality of delivery catheters, in which the stent-grafts are respectively initially positioned in their radially-compressed states.

30. The method according to claim 16, wherein providing the stent-graft system comprises providing the stent-graft system in which the graft members are securely fixed to the stent members, respectively, such that the circumferential arc extents are less than the entire circumferences of the respective stent members along at least 80% of the respective axial lengths of the stent members, when the stent-grafts are in their radially-expanded states.

31. The method according to claim 30, wherein providing the stent-graft system comprises providing the stent-graft system in which the graft members are securely fixed to the stent members, respectively, such that the circumferential arc extents are less than the entire circumferences of the respective stent members along the entire respective axial lengths of the stent members, when the stent-grafts are in their radially-expanded states.

* * * * *